US005526675A

United States Patent [19]
Ratton

[11] Patent Number: 5,526,675
[45] Date of Patent: * Jun. 18, 1996

[54] METHOD AND APPARATUS FOR MEASURING EVAPORATIVE EMISSIONS IN A FIXED-VOLUME ENCLOSURE

[75] Inventor: Kenneth Ratton, Farmington Hills, Mich.

[73] Assignee: Power-Tek, Inc., Farmington Hills, Mich.

[*] Notice: The portion of the term of this patent subsequent to Apr. 26, 2013, has been disclaimed.

[21] Appl. No.: 349,809

[22] Filed: Dec. 6, 1994

Related U.S. Application Data

[63] Continuation-in-part of Ser. No. 53,086, Apr. 26, 1993, Pat. No. 5,369,976.

[51] Int. Cl.$^6$ .................................................. G01M 19/00
[52] U.S. Cl. .......................................... 73/23.2; 73/118.1
[58] Field of Search ............................. 73/118.1, 116, 73/23.2, 23.31, 23.35, 40, 49.7

[56] References Cited

U.S. PATENT DOCUMENTS

| | | | |
|---|---|---|---|
| 3,942,357 | 3/1976 | Jenkins | 73/23.2 |
| 4,847,790 | 7/1989 | Suzuki et al. | 364/558 |
| 5,214,957 | 6/1993 | Collins | 73/40 |
| 5,369,976 | 12/1994 | Ratton | 73/23.2 |

Primary Examiner—Richard Chilcot
Assistant Examiner—George M. Dombroske
Attorney, Agent, or Firm—Westman, Champlin & Kelly

[57] ABSTRACT

Provided is a method and apparatus for measuring evaporative vehicle emissions in a fixed-volume enclosure. The method comprises the steps of providing a volume compensation means in fluid communication with a test chamber for compensating for changes in the test chamber fluid volume, where n is a positive integer, measuring the temperature of the test chamber fluid at the sample times $t_n$, measuring the absolute fluid pressure of fluid at the sample times $t_n$, determining the density of the evaporative emissions and the test chamber fluid at selected sample times $t_n$, determining the mass of evaporative emissions present in the chamber, determining the theoretical volume change of the test chamber fluid at said sample times $t_n$ in accordance with the Ideal Gas Law ($PV=nRT$), determining the mass of the evaporative emissions in aspirated volume, summing the determined masses of the evaporative emissions to provide a calculation of the evaporative emissions aspirated by the volume compensation means during expansion of the test chamber fluid, and summing this with the final sample mass to determine the total evaporative emissions from a vehicle. In an alternative embodiment, a plurality of impingers are also provided for use in determining the aspirated mass of alcohol emissions in flexible fueled vehicles.

1 Claim, 4 Drawing Sheets

$V_{TOTAL} = \int V dt$

METHOD AND APPARATUS FOR MEASURING EVAPORATIVE EMISSIONS IN A FIXED-VOLUME ENCLOSURE

RELATED APPLICATION

This application is a continuation-in-part of U.S. patent application Ser. No. 08/053,086, filed Apr. 26, 1993, U.S. Pat. No. 5,369,976 herein incorporated by reference in its entirety.

TECHNICAL FIELD

This invention relates generally to sealed housings for evaporative determination. More specifically, this invention relates to a method and apparatus for measuring evaporative vehicle emissions in a fixed-volume enclosure.

BACKGROUND OF THE INVENTION

As used in the art, the acronym "SHED" generally refers to Sealed Housings for Evaporative Determination. It should be noted that a "fixed volume SHED" refers to a SHED which has rigid panels and an aspiration style volume compensation system as described more fully in U.S. patent application Ser. No. 08/053,086. These SHEDS are generally rectangular enclosures which define fluid-fillable test chambers adapted to measure evaporative emissions such as hydrocarbon from automobiles, trucks and other motor vehicles. Historically, such testing was performed while the test chamber fluid (typically air) was maintained at a constant temperature. In operation, the test vehicle was placed in the SHED with the engine and all other equipment turned off. The door to the SHED was then closed and sealed. Thereafter, selected emissions such as hydrocarbon (HC) were measured at the beginning and end of a fixed timed period which was generally one hour. The SHED test is one step of the federal test procedure which is described in the Federal Register, subpart B, 86.101 to 86.145-82.

Those skilled in the art will recognize that regulations developed for the Clean Air Act have revised the evaporative portion of the federal test procedure. As revised, the evaporative portion now requires the use of a variable-temperature test chamber. As more thoroughly described in 40 CFR, § 86–99, as Revised Jul. 1, 1993, new SHEDS must define fluid-fillable test chambers capable of changing fluid temperature following prescribed fluid temperature profiles.

It should be noted that sealing technology, which was not a significant issue under the prior art constant temperature systems, has now become a complex problem for SHED designers under the variable temperature requirements. As those skilled in the art will recognize, by design, conventional SHEDs must include a plurality of penetrations for sample ports and temperature probes as well as a vehicle entrance/exit door, an operator egress door and a purge vent. All of these doors and penetrations must be sufficiently sealed or leakage will occur and emission sample will be lost. Because of the new variable temperature requirements and the need for a sealed housing to prevent unaccounted for loss of emissions, the corresponding volume compensation requirement was introduced to avoid pressurizing the SHED and possibly affecting evaporative emissions of the vehicle being tested.

To comply with the evaporative emissions measurement requirements, conventional SHEDs have incorporated various volume control devices for varying the volume of the fluid-fillable test chamber during expansion and contraction of test chamber fluid. Typically, such devices have been provided in fluid communication with the fluid (typically air) outside of the test chamber and are controlled by pure pressure feedback systems through the use of differential pressure transducers. Typical volume compensation devices include, for example, a plurality of inflatable bags which are disposed on the internal walls of the test chamber. Air is pumped in and out of the bags based on the pressure differential between the inside and outside of the test chamber. During expansion of the test chamber fluid, the bags are deflated to increase the volume of the test chamber. Similarly, during contraction cycles, the bags are inflated to decrease the volume of the test chamber.

In this prior art method, in order to measure the evaporative emissions levels in the test chamber, it is required to know the volume of air in the test chamber at the beginning of the test. For this purpose, an air flow meter is utilized to measure the amount of air pumped into and out of the bags disposed in the SHED. At the beginning of the test, the bags are evacuated and reinflated to a known volume. The volume of the SHED environment is then calculated by subtracting the known bag volume from the rigid enclosure volume. This volume is then "latched". The mass of air in the SHED will then be known and the evaporative emissions could then be measured directly from the environment at any point in the test. This method could potentially alleviate the loss of any evaporative emissions from the chamber, which renders the direct measurement of emissions in the SHED to be the same as it was with the previous constant temperature test. It should be noted, however, that because this method incorporates use of differential pressure transducers as feedback, a near-perfect seal is required for the SHED to operate properly. Indeed, leaks, however slight, will bias the differential pressure transducer and cause an error in the amount of volume compensation. Any error in volume compensation will result in an error in the measured evaporative emissions. The resulting error is created by forcing unaccounted for fluid out of the SHED or diluting the sample by drawing unaccounted for fluid into the SHED. Because truly "sealed" housings are nearly impossible to achieve, the pressure control systems of the prior art have proven unreliable and thus highly susceptible to error.

As those skilled in the art will recognize, the need for perfect sealing arises only because of the fear of emission sample loss. Thus, if a control system could be designed to precisely calculate emission loss or aspiration, a fixed-volume test chamber could be utilized and SHED pressurization could be obviated by merely providing or evacuating fluid directly from the SHED test chamber.

DISCLOSURE OF INVENTION

It is an object of the present invention to overcome the limitations of the prior art by providing a leak-tolerant apparatus and method for measuring evaporative vehicle emissions in a fixed-volume test chamber subject to fluid temperature changes.

In accordance with the invention, there is provided a housing having an interior portion defining a fixed volume fluid-fillable test chamber and an exterior portion. A fluid temperature sensor and a fluid pressure sensor are provided in communication with the test chamber fluid. Fluid conditioning means are provided in communication with the test chamber for controlling the temperature of the test chamber fluid. Volume compensation means are also provided in communication with the test chamber for measuring compensation of changes in test chamber fluid volume.

Also, in accordance with the invention, there is provided a measurement means such as a Flame Ionization Detector for measuring hydrocarbon levels in a fixed-volume test chamber. The fixed volume test chamber is filled with a fluid having a predetermined mass of evaporative emissions, at a certain temperature and pressure at time $t_0$. The claimed method comprises the steps of providing volume compensation means in communication with the test chamber for compensating for changes in test chamber fluid volume. Thereafter throughout the test, the density of evaporative emissions in the test chamber fluid must be determined in mass per unit volume at selected sample times $t_n$, where n is a positive integer. Also at time $t_n$, the temperature of the test chamber fluid must be measured along with the absolute fluid pressure of the test chamber fluid. Thereafter, for positive changes in volume, the mass and therefore density of the sample at each time $t_n$ may be determined. The density of the sample at time $t_n$ is averaged with the density of the previous sample $t(n-1)$ and multiplied by the change in volume over the same time period. The result is summed with subsequent results to provide a calculation of the sample aspirated by the volume compensation means during expansion of the test chamber fluid. This aspiration calculation summed with the final determined sample mass will result in the total evaporative emissions from the emissions source.

In the alternative embodiment referenced above, three (3) impingers are utilized to determine the alcohol concentration of the test chamber fluid during three corresponding time periods i.e. at the start of the test, throughout the test and at the completion of the test. By subtracting the determined alcohol concentration at the beginning of the test from the determined concentration at the end of the test, the mass of alcohols emitted may be calculated. This mass, added to the mass aspirated during the test (the mass trapped in the second impinger) yields the total evaporated alcohol emissions during the test.

The above objects and other objects, features, and advantages of the present invention are readily apparent from the following detailed description of the preferred embodiments of the invention when taken in connection with the accompanying drawings.

BEST MODES FOR CARRYING OUT THE INVENTION

Figure 1:
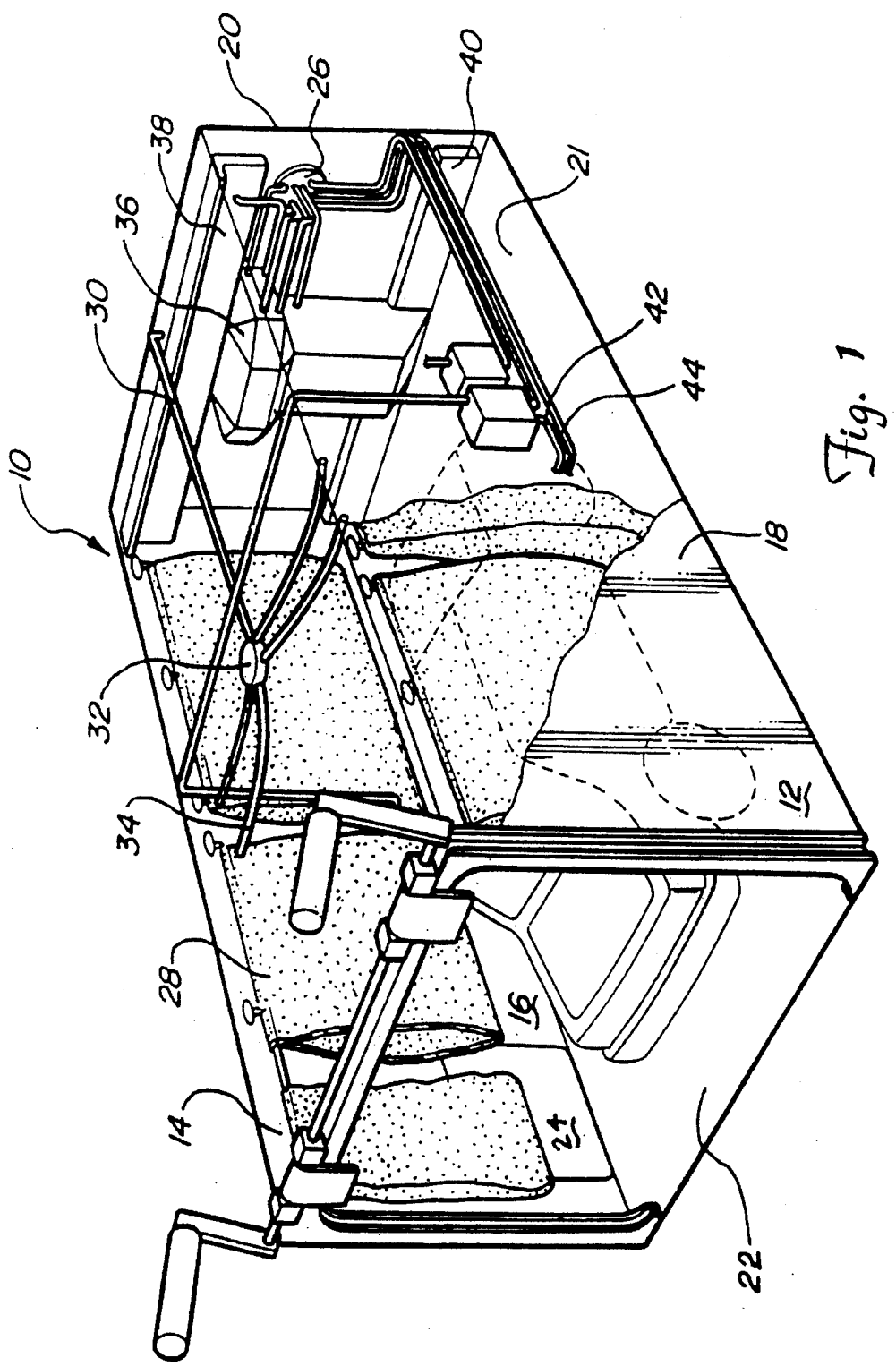
FIG. 1 is a perspective view of a prior art vehicle test chamber.

Referring to FIG. 1, a prior art variable-volume Sealed Housing For Evaporative Determination (SHED) is shown generally indicated by reference numeral 10. SHED 10 is a generally rectangular enclosure having a bottom portion 12, a top portion 14, side portions 16 and 18 and a rear portion 20. A vehicle entrance/exit door 22 is also provided to define a fluid-fillable test chamber 21. SHED 10 further includes an operator egress door 24 and a plurality of penetrations 26 for sample ports, temperature probes and the like. Still further, prior art SHED 10 includes a plurality of air-expandable and partially air-filled bags 28 provided in fluid communication with an external pumping means (not shown) through tubing 30, manifold 32 and branch tubing 34.

Still referring to FIG. 1, there is shown a heating, and cooling means 36 in communication with air supply plenum 38 and return air plenum 40. SHED 10 further includes a pair of temperature sensing devices, one of which is shown and designated by reference numeral 42. As shown, bags 28 provide variable-volume capability and have historically been controlled through the use of pure pressure feedback control systems which determine the differential pressure between the test chamber fluid and the fluid outside of SHED 10. In operation, bags 28 are inflated or deflated so as to decrease or increase the test chamber volume accordingly.

Figure 2:
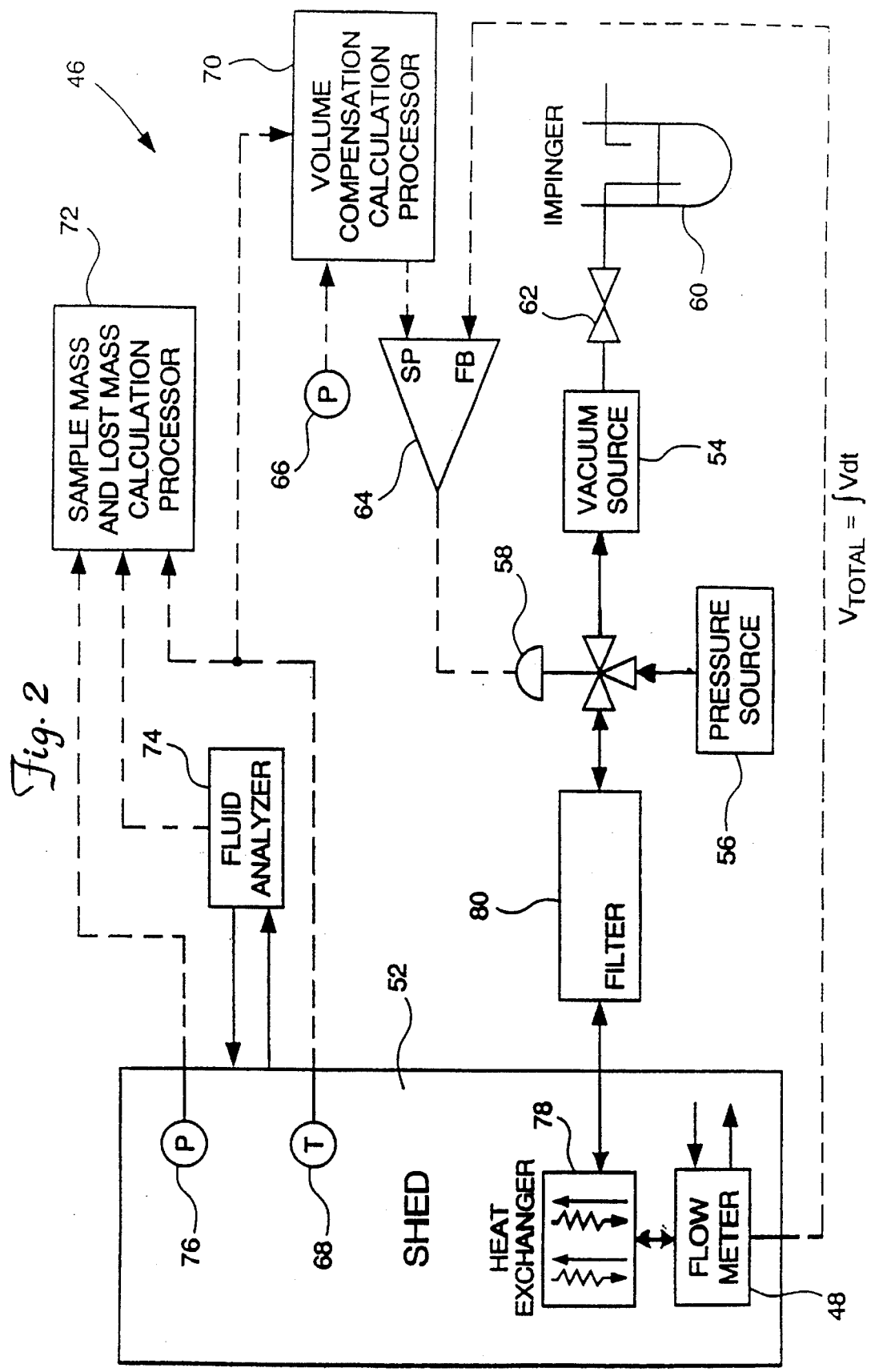
FIG. 2 is a schematic diagram of the measurement system of the present invention.

Turning now to FIG. 2, there is shown a schematic diagram of the emissions measurement system 46 of the present invention in conjunction with a preferred fixed volume control system. As shown, in the preferred embodiment, the volume control system includes a flow metering device 48 which is provided in fluid communication with the test chamber 52. The flow metering device 48 is further provided in fluid communication with a vacuum source 54 for evacuating fluid from the test chamber 52 during expansion cycles. Similarly, the flow metering device 48 is provided in fluid communication with a pressure source such as pump 56 which is preferably a filtered or zero air source for providing filtered fluid, free from selected contaminants (i.e. at least the constituents sought to be measured) to the test chamber during contraction cycles. As shown, flow metering device 48 is used as feedback for the volume compensation loop. As the air in test chamber 52 changes temperature, the volume compensation calculation will determine the total mass of air required to be in the test chamber to maintain a zero differential pressure. This calculated mass is then compared to the total mass of air plus that measured by the flow metering device 48 to have been drawn into or expelled from the test chamber 52. A correction will be made in the setting of control valve 58 to correct for any difference.

There is also provided in the preferred volume control system a controller 64 in electrical communication with volume compensation processor 70 and flow metering device 48 via a feedback loop. In turn, processor 70 is in electrical communication with an externally disposed pressure sensor and an internally disposed temperature sensor 66 and 68, respectively. Alternatively, the pressure sensor may be disposed within the chamber.

Still referring to FIG. 2, there is provided an emissions measurement system of the present invention which includes a sample and aspirated mass processor 72 in electrical communication with a fluid analyzer 74, temperature sensor 68, and an internally disposed pressure sensor 76 for determining the emission sample mass and for calculating aspiration. As described more fully below, fluid analyzer 74 may comprise, for example, a Flame Ionization Detector (FID), a Fourier Transform Infrared analyzer (FTIR), or any other suitable fluid analyzer. These analyzers are used to determine the amount of evaporative emissions present in the test chamber 52 during the test. In operation the sample is drawn into fluid analyzer 74, analyzed and returned to test chamber 52. Processor 72 determines the sample mass and aspirated mass during the test. In keeping with the invention, those skilled in the art will recognize that if an FTIR is selected as the fluid analyzer, PPM HC and PPM alcohol as well as any other constituent present in air may be determined. A plurality of impingers may also be used in conjunction with fluid analyzer 74 when testing flexible fueled vehicles.

With reference still to FIG. 2, in one preferred embodiment, the emissions measurement system of the present invention further includes an internally disposed heat exchanger 78 and a filter 80. Heat exchanger 78 is used to ensure that any fluid that passes the flow metering device 48 is at the same temperature as the fluid in the rest of test chamber 52. It should be noted, however, that in an alternative embodiment, a temperature correction can be made to obviate the need for a heat exchanger. Still further, in yet another alternative embodiment adapted for use in measuring flex fuel vehicles, there is further provided a quick disconnect 62 for replacing impinger 60. As explained in further detail below, for each flex fuel tests, there must actually be three (3) impingement samples. The first sample would be to determine the background alcohol level present at the beginning of the test. Similarly, the second sample would be taken with a "large impinger" to determine the alcohol aspirated from test chamber 52 during the test due to the expansion of air. Finally, the third sample would be taken to determine the mass of constituents being measured at the end of the test. The difference between the determined masses of samples 1 and 3 summed with the determined mass of sample 2 yields the total mass emitted from the vehicle.

Figure 3:
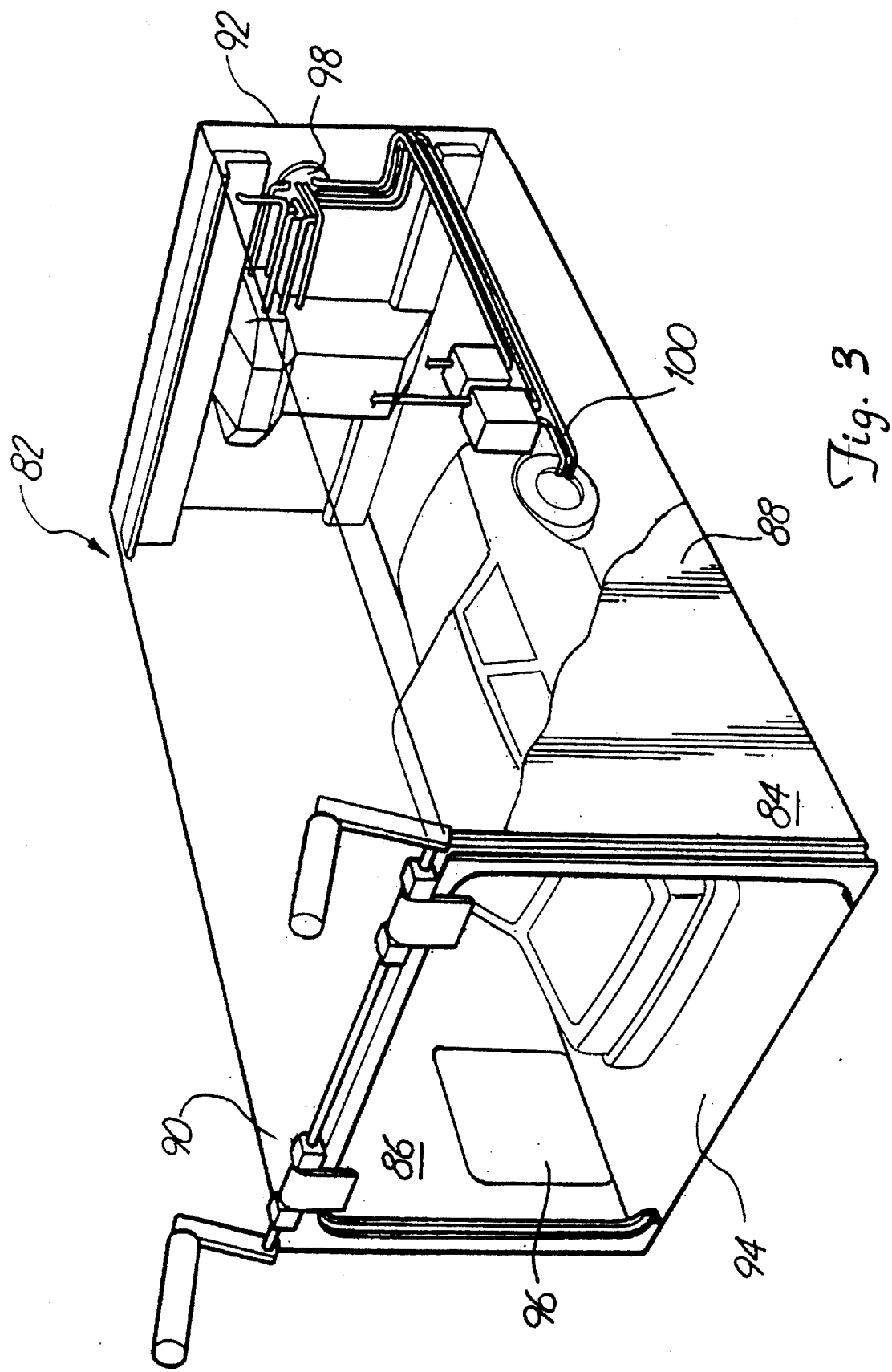
FIG. 3 is a perspective view of an emissions measurement SHED for use with the present invention.

With reference now to FIG. 3, a sealed housing defining a fixed-volume test chamber and incorporating the control system of the present invention is shown generally designated by reference numeral 82. Like prior art SHED 10, SHED 82 is also rectangular in shape and includes a bottom portion 84, side portions 86 and 88, top portion 90 and rear portion 92. SHED 82 further includes a vehicle entrance/exit door 94, an operator egress door 96 and a plurality of penetrations 98 which are provided for sample ports, temperature probes such as RTD 100, and the like. SHED 82 also includes volume compensation means which comprise flow metering devices (not shown) of the type referenced in FIG. 2 and control means (not shown) such as a feedback control circuit. In operation, as the test chamber fluid expands, fluid ($V_n$) will be evacuated from the test chamber, as determined in accordance with the ideal gas law ($PV=nRT$). This fluid volume V. contains a mass of emission sample ($M_n$), which may similarly be determined as described more thoroughly below. By summing the total determined masses ($M_n$) of evaporative emissions evacuated during expansion of the test chamber fluid with the measured evaporative emissions present in the chamber at the end of the test, the total mass of evaporative emissions emitted during the test is calculated.

Significantly, the control system of the present invention is directed for use in a fixed-volume test chamber and thus obviates the need for an internal volume compensation device such as the wall-mounted inflatable bags of the prior art. In operation, test chamber fluid is allowed to escape and the mass of evaporative emissions contained therein is calculated as an aspiration factor. The disclosed control system is truly leak-tolerant as it only relies on the physics of the fluid and does not rely on an accurate volume control system to determine the total evaporative emissions.

Method Of Operation

Figure 4:
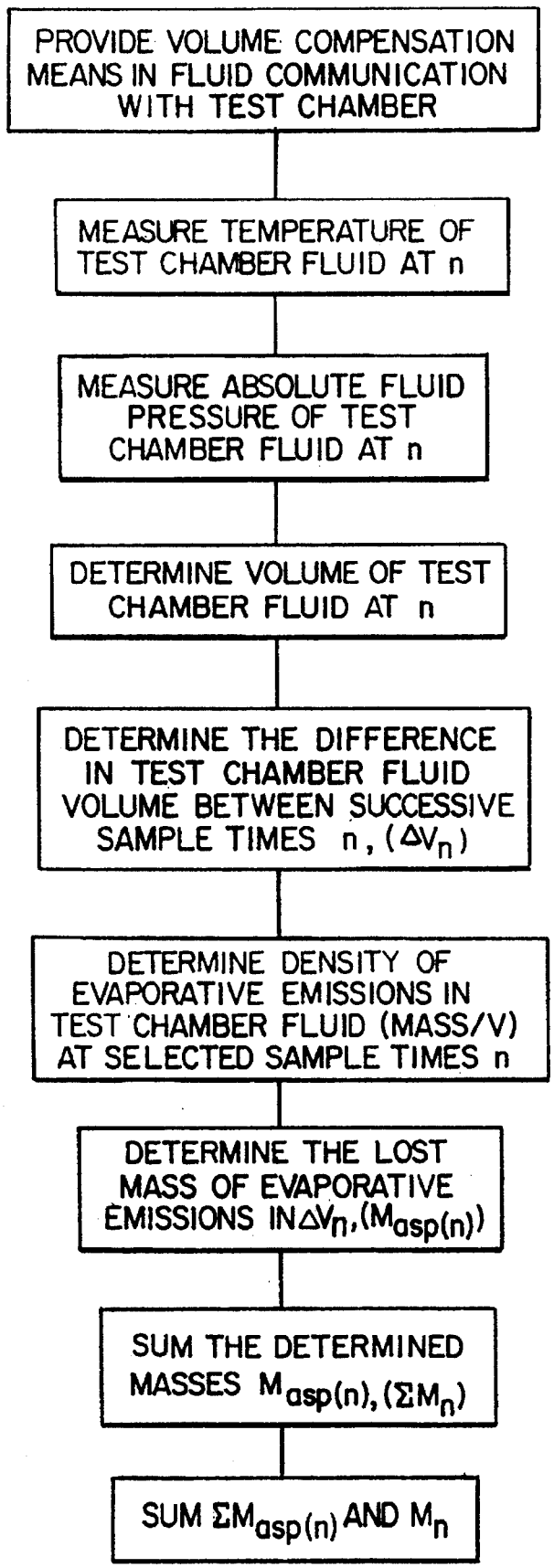
FIG. 4 is a block diagram of the method steps of one preferred embodiment of the present invention.

Referring now to FIG. 4, the method of operation of the emissions measurement system of the present invention will be described in further detail. As shown in FIG. 4, for each discrete time interval, the absolute fluid pressure of the test chamber must be determined along with the test chamber temperature and the concentration of the evaporative emissions sought to be measured. In the case of hydrocarbon emissions, those skilled in the art will recognize that hydrocarbon mass may be determined in accordance with the following formula:

$$M_n = kV_{fixed} 0.0001 \text{ (3)} \left[ \frac{CHC_n P_n}{T_n} - \frac{CHC_1 P_1}{T_1} \right]$$

where,

M=Hydrocarbon mass (gm)
CHC=Hydrocarbon concentration (PPM carbon)
$V_{fixed}$=Fixed enclosure volume (Ft$^3$)
P=Barometric pressure (in Hg)
T=Enclosure air temperature (R)
K=3.05 English units (changes depending on the mass ratio of the HC being measured)
n=Positive integer indicating sample sequence Where the HC concentration is determined using a Flame Ionization Detector (FID), Fourier Transform Infrared Analyzer (FTIR) or other suitable means. In the case of an FID analyzer, for example, the sample pump is adapted to draw sample out of the test chamber 52, pass a small portion of the sample through the flame and return the sample back to the test chamber. The FID output is normally proportional to PPM (Parts Per Million parts of air) HC. The results from this calculation yields mass of hydrocarbon in the test chamber 52 at any point in time not including aspirated HC mass due to expansion. Thereafter, the density at a selected sample time may be calculated in accordance with the formula:

$$\rho_n = M_n/V_{fixed} = \text{Density of emissions at any time (gm/ft}^3\text{)}.$$

Once determined, correction of the data for positive changes in volume must then be made using the Ideal Gas Law:

$$\Delta V_n = \frac{V_{fixed} P_{n-1} T_n}{T_{n-1} P_n} - V_{fixed}$$

where, $\Delta V_{tn}$=Change in volume at n (Ft$^3$)
$V_{fixed}$=Fixed volume of SHED minus vehicle (Ft$^3$)
$P_{n-1}$=Pressure at previous reading (in Hg)
$P_n$=Pressure at n (in Hg)
$T_{tn}$=Temperature at n (R)
$t_{n-1}$=Temperature at previous reading (R)

The total mass of emissions at any time may now be calculated as follows:

$$M_{asp(n)} = \Delta V_n * (\rho_n + \rho_{n-1})/2.0$$

$$M_{total(n)} = \sum_{n=2}^{n=n} M_{asp(n)} + M_n - M_1$$

Where, $M_{aspt}$=Mass of emissions aspirated at time t
$\Delta V_{t(n)}$=Change in volume at time t
$\rho_{t(n)}$=Density of emissions at time t
$\rho_{t(n-1)}$=Density of emissions at previous calculation (t−1)
$M_1$=Initial background evaporative emission
$M_{totalt}$=Total mass of emissions to present time t
$M_t$=Mass of emissions in chamber as measure by the analyzer at time t
n=a positive integer variable The volumetric processing steps are thoroughly described in co-pending U.S. patent application Ser. No. 08/023,322, filed Feb. 26, 1993, which is commonly owned. The disclosure of Ser. No. 08/023,322 is expressly incorporated herein by reference.

As indicated above, an FTIR analyzer may also be used in place of a FID analyzer. In such case, HC as well as methanol and/or ethanol concentrations of alternative fuels may be determined in much the same way as with a FID analyzer. In operation, the sample is again drawn from test chamber 52 of FIG. 2 during the test. Because the FTIR analyzer may be used to determine both HC and alcohol emissions, it is recognized that the analyzer must be set up initially to indicate the total concentration of the evaporative constituent which is of interest. For example, in the case of flexible fueled vehicles, the total HC and total methanol or ethanol concentration would be of interest. Therefore, these measurements should be read and indicated by the analyzer in units of PPM. Significantly, the calculations for alcohol blend fuels are the same as those used for standard fuels. In operation, the system is designed to convert the PPM into density in mass per unit volume mixture, account for aspirated volume and multiply the same by the density resulting in aspirated mass. The aspirated mass is summed over the test duration. This summed aspirated mass is added to the evaporative emissions mass left in test chamber 52 of FIG. 2 at the end of the test as indicated by the last concentration sample yields the total evaporative emission from the vehicle during the test.

In an alternative embodiment, alcohol emissions from flexible fueled vehicles, such as methanol or ethanol blend fueled vehicles, may be determined through the use of impingers. As those skilled in the art will recognize, an impinger is a water bath that fluid (generally air) is bubbled through to expose the fluid to water. Because alcohol has a higher affinity for water than air, applicants have found that any alcohol present in the air drawn out of test chamber 52 is dissolved accordingly. Thus, the mass of alcohol lost during expansion of the test chamber air may be determined in cooperation with a Gas Chromatograph (GC) as described more thoroughly below.

In this method, at the beginning of the test, a sample of the concentration of alcohol in the test chamber 52 of FIG. 2 is taken and passed through a first impinger 60 at a selected flow rate for a selected amount of time. Thereafter, the first impinger 60 is removed and a second "large impinger" (not shown) is connected in its place. This "large impinger" remains attached to the test chamber 52 via outlet 62 of the volume compensation device. In operation, air removed from the test chamber 52 passes through the large impinger which traps any alcohols present in the impinger water. This effectively continuously integrates the lost mass of alcohol over the entire test much like the calculations for the FID approach. The use of two impingers will ensure 100% alcohol absorption. In keeping with the invention, during contraction of the test chamber air, air is passed into the test chamber 52 bypassing the impinger since no sample is being aspirated during these cycles. At the end of the test, the large impinger is removed and a third impinger (not shown) is put in its place. Again, a sample is drawn from the test chamber 52 for a specific amount of time and flow rate. This sample, when analyzed, will indicate the concentration of alcohol in the test chamber left at the end of the test. As referenced above, the concentration found at the beginning of the test is then subtracted from the concentration at the end of the test. Thereafter, the mass of the alcohols emitted is calculated. This mass emitted added to the aspirated mass trapped in the large impinger will yield the total evaporated alcohol emissions during the test.

Significantly, the impinger samples are analyzed using a Gas Chromatograph (GC). As those skilled in the art will recognize, a Gas Chromatograph is not a continuous sampling system. Thus the samples must be taken and analyzed separately to determine the mass of alcohol per unit sample mass. In operation, the GC will determine the entire chemical breakdown of the mass of each constituent dissolved in the fluid which is sought to be analyzed. For example, a 15 ml impinger may be used to analyze a 0.5 ml sample of water in cooperation with a GC. If the sample contained 0.01 mg of alcohol, it is recognized that 0.3 mg of alcohol will be present in the impinger. (0.01 mg/0.5 ml alcohol *15 ml=0.3 mg alcohol). In accordance with the invention, if the 15 ml impinger reference above was the second or "large impinger" then the 0.3 mg alcohol would account for all of the alcohol aspirated from the test chamber during the test. Similarly, if the 15 ml impinger was used at the end of the test, then the determined mass of alcohol would have to be divided by the total volume of air drawn into the impinger. For example, consider an impinger which has had 0.2 CFM of air passed through it during an 1800 second time period (6 cubic feet of air). If it is determined that 0.3 mg of alcohol are present in the impinger at the end of the test, then there must be 0.3 mg of alcohol per 6 cubic feet of test chamber air. If the test chamber has a volume of 1500 cubic feet, then 75 mg of alcohol must have been present in the test chamber at the end of the test.

While the best modes for carrying out the invention have been described in detail, those familiar with the art to which this invention relates will recognize various alternative designs and embodiments for practicing the invention as defined by the following claims.

What is claimed is:

1. A leak-tolerant method of measuring evaporative emissions in a fixed volume test chamber filled with a fluid having a predetermined mass of evaporative emissions $M_1$, chamber volume, temperature and pressure at time $t_0$ and a determined mass ($M_n$) of evaporative emissions at a reading $t_n$, comprising the steps of:

providing volume compensation means in fluid communication with said test chamber for compensating for changes in said test chamber fluid volume;

measuring the temperature of said test chamber fluid at said sample times $t_n$;

measuring the absolute fluid pressure of said test chamber at said sample times $t_n$;

determining the mass of evaporative emissions present in the chamber;

determining the density of said evaporative emissions in said test chamber fluid in mass per unit volume at selected sample times $t_n$, where n is a positive integer;

determining the theoretical volume change of said test chamber fluid at said sample times $t_n$ in accordance with the Ideal Gas Law (PV=nRT);

determining the aspirated mass of said evaporative emissions in $M_{asp(n)}$;

summing the determined masses of said evaporative emissions $M_{asp(n)}$ to provide a calculation of the total evaporative emissions aspirated by said volume compensation means during expansion of said test chamber fluid, ($\Sigma M_{asp(n)}$); and summing ($\Sigma M_{asp(n)}$) and $M_n$, and subtracting $M_1$ to determine a total mass of evaporative emission.

* * * * *